( 12 ) United States Patent
Dahl et al.

(10) Patent No.: US 6,901,289 B2
(45) Date of Patent: May 31, 2005

(54) SYSTEM FOR PROVIDING ELECTRICAL STIMULATION TO A LEFT CHAMBER OF A HEART

(75) Inventors: Roger Dahl, Andover, MN (US); Thomas M. Soukup, Plymouth, MN (US); Joe Perttu, Chanhassen, MN (US); Arnold Thornton, Roseville, MN (US); Elisabeth L. Belden, Maple Grove, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 533 days.

(21) Appl. No.: 10/034,905

(22) Filed: Dec. 28, 2001

(65) Prior Publication Data

US 2002/0111663 A1 Aug. 15, 2002

(Under 37 CFR 1.47)

Related U.S. Application Data

(60) Provisional application No. 60/258,651, filed on Dec. 29, 2000.

(51) Int. Cl.[7] .............................................. A61N 1/365
(52) U.S. Cl. ........................................................ 607/9
(58) Field of Search .......................... 607/4–9, 116–128; 600/373–375

(56) References Cited

U.S. PATENT DOCUMENTS

| 4,161,952 | A | 7/1979 | Kinney et al. ............... 128/786 |
|---|---|---|---|
| 4,506,680 | A | 3/1985 | Stokes .......................... 128/786 |
| 4,577,642 | A | 3/1986 | Stokes .......................... 128/784 |
| 4,606,118 | A | 8/1986 | Cannon et al. ................ 29/825 |
| 4,711,251 | A | 12/1987 | Stokes ......................... 128/784 |
| 5,090,422 | A | 2/1992 | Dahl et al. .................... 128/784 |
| 5,246,014 | A | 9/1993 | Williams et al. ............. 607/122 |
| 5,387,233 | A | 2/1995 | Alferness et al. ............ 607/126 |
| 5,466,252 | A | 11/1995 | Soukup et al. ............... 607/116 |
| 5,545,183 | A | 8/1996 | Altman ........................... 607/5 |
| 5,957,970 | A | 9/1999 | Shoberg et al. .............. 607/722 |
| 5,964,795 | A | 10/1999 | McVenes et al. ............ 607/122 |
| 6,006,122 | A | 12/1999 | Smits ........................... 600/373 |
| 6,006,137 | A | 12/1999 | Williams ...................... 607/119 |
| 6,070,104 | A | 5/2000 | Hine et al. .................... 607/123 |
| 6,192,280 | B1 | 2/2001 | Sommer et al. ............. 607/122 |
| 6,256,541 | B1 * | 7/2001 | Heil et al. .................... 607/122 |

FOREIGN PATENT DOCUMENTS

EP           1 000 634 A1     10/1998     ............ A61N/1/39

OTHER PUBLICATIONS

Bakker et al., "Biventricular Pacing in Congestive Heart Failure," Clinical Research.

Blanc et al., "Evaluation of Different Ventricular Pacing Sites in Patients with Severe Heart Failure," *American Heart Association, Inc.*, 1997; 3273–3277.

(Continued)

*Primary Examiner*—George Manuel
(74) *Attorney, Agent, or Firm*—Michael C. Soldner; Girma Wolde-Michael

(57) ABSTRACT

A medical electrical lead is disclosed that is adapted for placement in the coronary sinus, or a branch vein thereof. The lead includes a first and second pace/sense electrode. A selection mechanism is provided to select either the first or the second electrode for use as a cathode, with the other electrode being selected as the anode. According to another aspect of the invention, a high-voltage coil electrode may be provided between the first and second electrodes. The coil electrode may be electrically coupled to the anode to increase the shadow area of the coil electrode.

34 Claims, 8 Drawing Sheets

OTHER PUBLICATIONS

Cazeau et al., "Heart Failure: Acute Hemodynamic Improvement Provided by Multisite Biventricular Pacing," *JACC* Feb. 1997; 111A.

Daubert et al., "Permanent Biventricular Pacing by a Transvenous Approach," *JACC* Feb. 1997; 431A.

Daubert et al., "Permanent Biventricular Pacing with Endocardial Leads: Is it Feasible?" Abstract.

Delfaut et al., "Comparison of Right Atrial Activation During Coronary Sinus Ostial Pacing with Dual Site Right Atrial and Biatrial Pacing," *JACC* Feb. 1997; 253A.

Dreifus et al., "Effect of Multiple Simultaneous Activation Sites (biventricular pacing) on Ventricular Depolarization and Ventricular Arrhythmias," 33–39.

Foster et al., "Improved Hemodynamics Achieved with Biventricular Pacing," *JACC* Feb. 1994; 156A.

Foster et al., "Acute Hemodynamic Effects of Atrio–Biventricular Pacing in Humans," Ann Thorac Surg 1995;59:294–300.

Guazzi et al., "Despite an Excellent Effect on Left Ventricular Performance, Carvedilol Fails to Improve the Pulmonary Function and Peak Exercise Uptake in Chronic Heart Failure. Any Link?" *JACC* Feb. 1998; 31A.

Leclercq et al., "Acute Hemodynamic Response to Biventricular DDD Pacing in Patients with Severe Conjestive Heart Failure and Without Conventional Indication for Permanent Pacemaker," *From the 70th Scientific Sessions*, 520.

Toshihide et al., "Effect of Pacing Site on Biventricular Contractility in In Vivo Canine Hearts," *Japanese Circulation Journal*; Sep. 1988, 52:987.

* cited by examiner

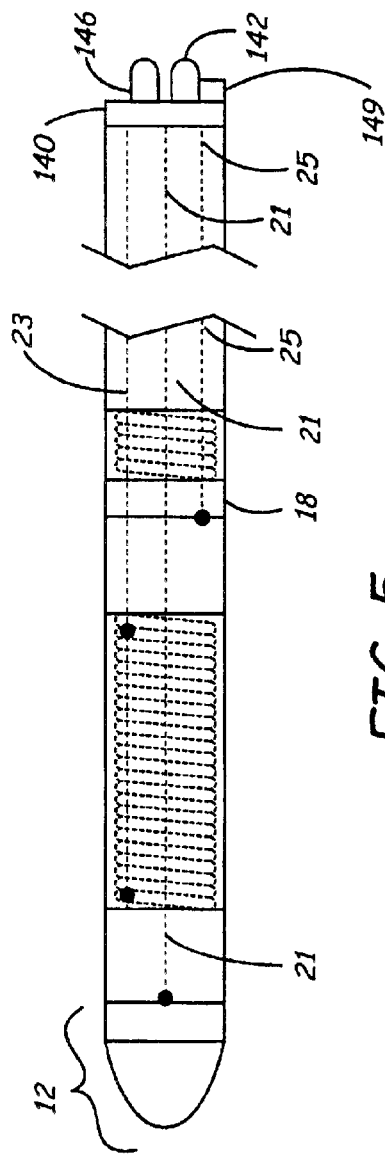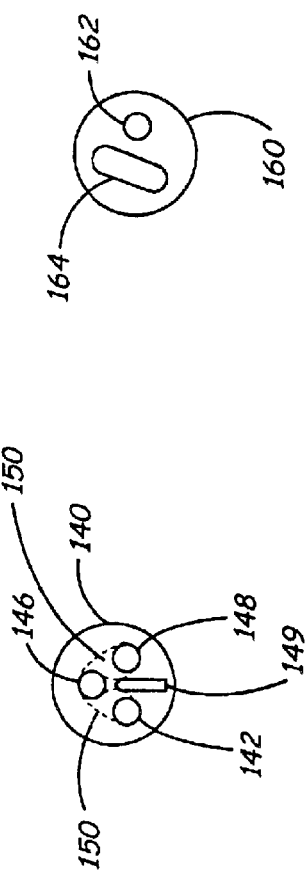
FIG. 5
FIG. 6
FIG. 7

SYSTEM FOR PROVIDING ELECTRICAL STIMULATION TO A LEFT CHAMBER OF A HEART

RELATED APPLICATIONS

This Application claims priority to provisionally-filed U.S. Patent Application Ser. No. 60/258,651 filed Dec. 29, 2000 entitled "Medical Electrical Lead", which is incorporated herein by reference in its entirety.

FIELD OF THE INVENTION

The present invention relates generally to an implantable medical electrical lead; and more particularly, relates to a medical electrical lead system for implantation in a cardiac vein.

BACKGROUND OF THE INVENTION

It has long been known that implantable medical electrical leads may be positioned transvenously within one or more chambers of the heart to provide electrical stimulation to, and to monitor signals occurring within, the cardiac tissue. In order to achieve reliable sensing of the cardiac electrogram and/or to apply stimulation that effectively paces or cardioverts the heart chamber, it is necessary to accurately position the electrode surface against the endocardium or within the myocardium at the desired site and affix it during an acute post-operative phase until fibrous tissue growth occurs. After implantation, the leads may be coupled to an implantable medical device (IMD) such as a pacemaker or cardioverter/defibrillator so that the desired stimulation may be provided to the cardiac tissue.

More recently, endocardial pacing and cardioversion/defibrillation leads have been developed that are adapted to be advanced into the coronary sinus and branch coronary veins. During this type of implant procedure, a distal end of a lead is advanced through the superior vena cava and the right atrium, and through the ostium of the coronary sinus. The lead may further be advanced within the coronary sinus into one of the branch veins.

Placement of leads within the coronary sinus and branch veins is important because these leads can be located adjacent to the left ventricle or the left atrium of the heart. Electrical stimulation can then be provided to the left chambers of the heart without actually placing one or more leads into these chambers. Because the left side of the heart accounts for the majority of the heart's hemodynamic output, various pathologies may be better treated through such left-heart stimulation. For example, in patients experiencing conditions associated with heart failure, electrical stimulation of both the right and left sides of the heart can be used to re-synchronize the depolarization of the left and right ventricles in a manner that increases the cardiac output.

In addition to providing important benefits to heart failure patients, the location of electrodes within the coronary sinus and branch veins can also reduce defibrillation thresholds. That is, when a shocking electrode is positioned within a left-sided cardiac vein and used in conjunction with other shocking electrodes placed in more traditional locations, a lower shock energy may be required during cardioversion and/or defibrillation therapy. This can reduce the discomfort associated with these therapies.

Several challenges are posed by providing both pacing and defibrillation electrodes within the coronary vasculature. Because of the small vessel size, positioning multiple leads within the vasculature is difficult. Additionally, the size of coil electrodes of the type needed for high-voltage therapies may be limited based on the size of the vessels, thereby limiting the area of the tissue through which current flows during the therapy. This may limit the efficacy of high-voltage therapies. Finally, locating the leads at a precise location needed to provide adequate tissue stimulation may be difficult given the problems associated with navigating the torturous vessels such as the coronary sinus and branch veins.

What is needed, therefore, is an improved system that may be used to provide both pacing and high-voltage therapy to the left chambers of the heart and that may be reliably fixed within a branch vein of the coronary sinus.

SUMMARY OF THE INVENTION

According to one embodiment of the current invention, a medical electrical lead is disclosed that is adapted for placement in the coronary sinus, or a branch vein of the coronary sinus. The lead includes a first electrode located in proximity to the distal end of the lead. A second electrode is located distal to the first electrode. A selection mechanism is provided to select either the first or the second electrode for use as a cathode, with the other electrode being selected as the anode. In one embodiment, the selection mechanism may include a configurable circuit. Alternatively, the selection mechanism may include selectable electrical configurations provided by an adaptor module. After the selection is complete, relative low-voltage electrical stimulation, including pacing pulses, may then be delivered between the anode and cathode to a left chamber of the heart.

The lead of the current invention may include means to aid in the positioning of the lead within the coronary sinus or branch veins. For example, the lead may include a lumen formed within the lead body, or adjacent to an exterior surface of the lead. The lumen is adapted to receive a guidewire or stylet for use in delivering the lead to a target location during implant. In one embodiment, the lumen is formed of a collapsible tube such as tubing formed of a porous PTFE tubing material. The tube is carried adjacent to at least a portion of the outer surface of the lead body.

According to yet another aspect of the current invention, a coil electrode may be positioned between the first and second electrodes. The coil electrode is adapted to deliver relatively high-voltage therapy such as cardioversion/defibrillation shocks to the heart. In one embodiment, the coil electrode may be electrically coupled to the electrode selected as the anode to increase the shadow area of the coil electrode during high-voltage stimulation therapy.

In another embodiment of the invention, a method of delivering electrical stimulation to a heart is provided. The method includes the step of delivering a lead to a branch vein of the coronary sinus, wherein the lead includes first and second pace/sense electrodes coupled to a distal end of the lead. The method further includes selecting one of the first or the second pace/sense electrode as a cathode, and delivering electrical stimulation between the cathode and the other pace/sense electrode to a left chamber of the heart. The lead may further include a coil electrode for delivering relatively high-voltage stimulation to the heart. In this embodiment, the method may further include electrically coupling one of the pace/sense electrodes to the coil electrode prior to the delivery of the high-voltage therapy to increase the shadow area of the coil electrode.

In still another embodiment of the invention, a system is provided delivering electrical stimulation to a heart. The system includes a lead having first and second pace/sense electrodes, and a coil electrode. The system may further include an adapter for selecting one of the first and the second pace/sense electrodes as a cathode for delivery of pacing therapy. The adapter may further couple the other one of the pace/sense electrodes to the coil electrode for use as the anode, and further for delivery of relatively high-voltage stimulation. As an alternative to the adapter, the system may include an implantable medical device having means for selectably configuring the electrodes in the afore-mentioned manner.

Other scopes and aspects of the current invention will become apparent to those skilled in the art from the following description and the accompanying drawings.

BRIEF DESCRIPTION OF THE DRAWINGS

FIG. 5 is a side view of a lead that is similar to that shown in FIG. 2 including a multi-pin connector as may be used with the current invention.

FIG. 6 is an end view of the connector of FIG. 5.

FIG. 7 is an end view illustrating a mating interface for use with the connector of FIG.

DESCRIPTION OF THE INVENTION

The present invention provides a single lead system adapted for placement within a branch vein of the coronary sinus. This system is specifically sized to fit within the length and width of the branch vein.

Figure 1:
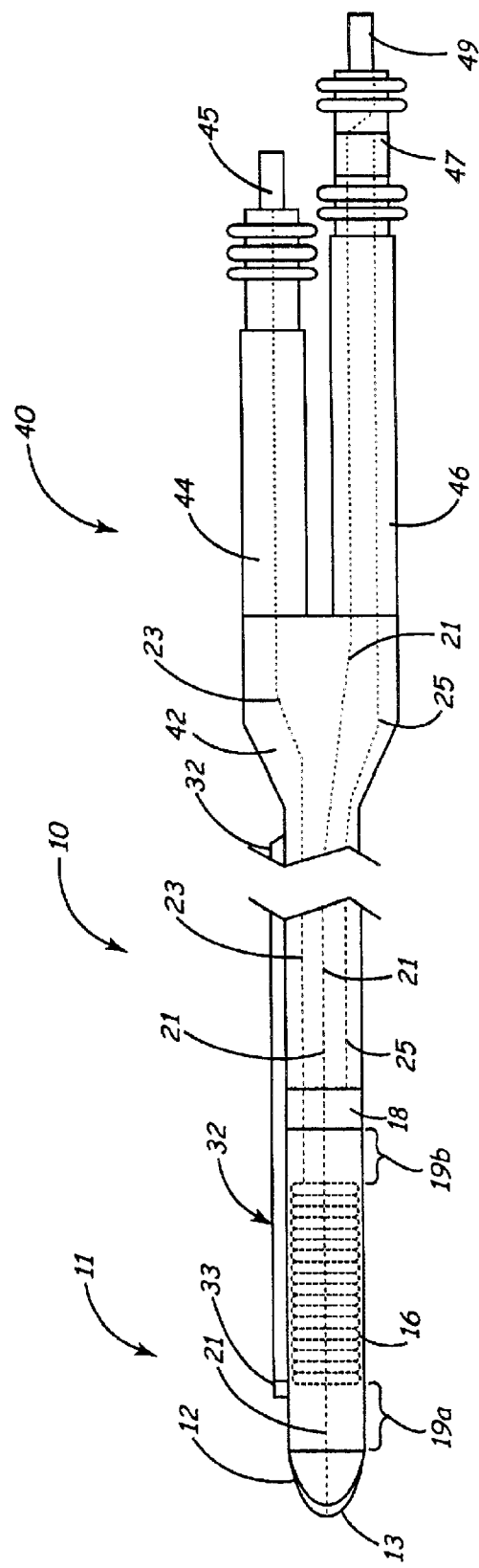
FIG. 1 is a plan view of one embodiment of the inventive lead system.

FIG. 1 is a plan view of one embodiment of the inventive lead system. The lead includes an elongated body 10 that may be of any conventional lead construction known in the art. For example, the exterior of lead may be formed of silicone, polyurethane, or a non-porous or dense PTFE.

The distal end of the elongated body includes a tip electrode 12 for pacing and sensing in the left ventricle. This electrode could be any of the various types of pacing electrodes known in the art such as a porous platinized electrode assembly. A tip electrode is shown, although a ring electrode located proximate the distal end of the elongate body 10 could be used in the alternative. In one embodiment, this electrode is a steroid-eluting porous pacing electrode, as described in commonly-assigned U.S. Pat. Nos. 4,506,680, 4,577,642; 4,606,118 incorporated herein by reference. The electrode may be constructed of porous, sintered platinum, titanium, or a similar bio-compatible metal.

Tip electrode 12 could include means to aid in fixing the electrode assembly at a desired site of implant within the branch vein. For example, the electrode could include flexible tine-like or fin structures. Fixation devices of this nature are disclosed in U.S. Pat. Nos. 5,964,795, 6,006,122, and 5,387,233 which are incorporated herein by reference. Alternatively, the lead body 10 could be shaped to have side-to-side undulations to wedge the lead within the vessel and aid in retaining the lead body at the implant site.

Shocking electrode 16, located proximal to tip electrode 12 provides cardioversion/defibrillation stimulation, and, in one embodiment, may be used as an anode for bipolar pace/sense therapy in conjunction with the pace/sense cathode, as will be discussed further below. Shocking electrode 16 is a coiled electrode that may be of any construction known in the art. In one embodiment, the coil is isodiametric with respect to the lead body. Such isodiametric electrode coils may be molded into the electrode body or the coils may be machined to provide a flush surface. This is described in U.S. Pat. No. 4,161,952, issued to Kinney et al. Similarly, U.S. Pat. No. 5,957,970 to Shoberg discloses an isodiametric defibrillation lead as may be used with the current invention. The lead described in the '970 patent is manufactured by removing a portion of an extruded tubular lead body in the region of the coil so that the electrode is flush with the surface of the lead.

Figure 2:
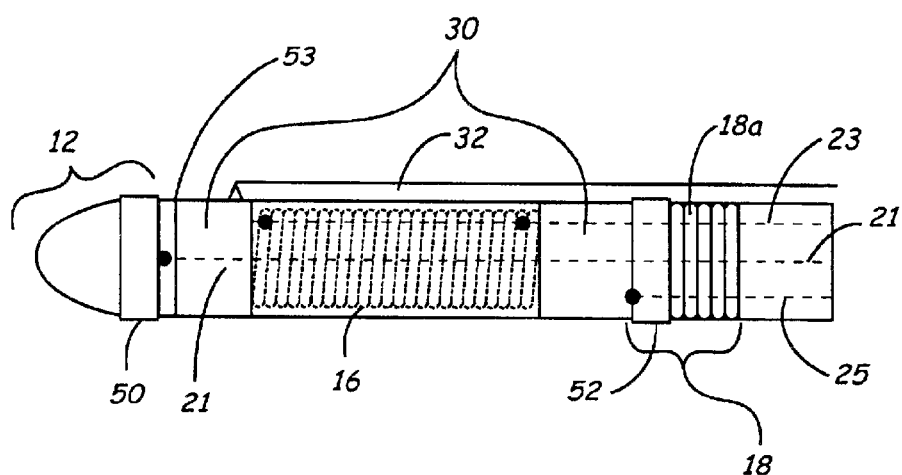
FIG. 2 is a side cutaway view of one embodiment of the distal portion of the lead.

Shocking electrode 16 may be encased in a layer of porous PTFE material or expandable PTFE (ePTFE), as shown in FIG. 2. The porous PTFE jacket 30 is designed to prevent tissue in-growth around the coils of the shocking electrode. Shocking electrode 16 is electrically coupled to a conductor 23 (shown dashed) extending to a connector pin 45 at the proximal end of the lead. The associated connector 44 may be of any type known in the art, including a DF-1 industry standard connector.

In one preferred embodiment of the current invention, elongate body 10 may further include a ring electrode 18. In FIG. 1, this electrode is shown located just proximal to the shocking electrode 16, although it may be positioned distal to the shocking electrode 16 in another embodiment. Pacing pulses may be delivered between tip electrode 12 and ring electrode 18. Additionally, ring electrode 18 may be used as the pace/sense cathode if the location of ring electrode is more favorable for such therapy than the most distal electrode. If the ring electrode 18 is selected as the pace/sense cathode, tip electrode 12 may be electrically coupled in common with the shocking electrode 16 to augment the shadow area of the shocking electrode. Similarly, if the most distal electrode 12 is selected to be the pace/sense cathode, the ring electrode 18 may be electrically coupled with the shocking electrode 16.

In the illustrated embodiment, conductors 21 and 25 extend to pin connector 49 and ring connector 47, respectively. Connector 46 may be any type of proprietary or industry-standard connector known in the art. For example, the connector may be an industry-standard IS-1 connector.

As noted above, the construction of the lead body may be of any type known in the art. Conductors 21, 23, and 25 may be of a cable or coil design, and may reside within individual lumens formed in the insulation. In another embodiment, one or more of the conductors may be coils positioned coaxially with respect to each other, with insulation provided between adjacent coils. In yet another embodiment, lead body 10 carries a drawn brazed stranded (DBS) cable insulated with FEP.

The lead body may further include a lumen for receiving a stylet. For example, one of the conductors 21, 23 and 25 may be coiled to define such a lumen, or the lumen may be formed within the insulation. In yet another embodiment, the lumen may extend through the distal end of elongate body 10 and tip electrode 12. In this instance, a guidewire may be advanced beyond the lead distal tip for positioning the lead body within the coronary sinus or a branch vessel. In this embodiment, a tip seal 13 may be provided at the distal end of the lumen, as described in commonly-assigned U.S. Pat. No. 6,192,280 incorporated herein by reference. This tip seal prevents the ingress of bodily fluids into the lumen.

According to one aspect of the invention, predetermined portions of the elongate lead body 10 may be coated at one or more locations with a porous Polytetrafluoroethylene (PTFE) material such as expanded PTFE (e-PTFE). As discussed in commonly-assigned U.S. patent application Ser. No. 09/827,103 filed Apr. 5, 2001 entitled "Implantable Medical Device Adapted to Promote Selected Tissue In-Growth and Method for Making the Same", incorporated herein by reference, porous PTFE having a relatively large pore size may be used to selectively promote tissue in-growth. Because of the tissue in-growth, portions of the lead coated with PTFE swell after implant. By selectively coating the lead body 10 in predetermined locations such as at locations 19a and 19b, this swelling effect urges electrodes 12, 16 and 18 against a vessel wall. This promotes capture, and retains the lead at a desired location of implant.

The lead body 10 of FIG. 1 is further shown having a side lumen 32 offset from the surface of the lead body. This side lumen may extend from the proximal lead end to any desired location at the distal end of the lead body. For example, the lumen may extend to tip electrode 12. This side lumen 32 may be formed of PTFE such that the inner lumen is collapsible. For example, a PTFE tube may be affixed to the lead body 10 using any type of bio-compatible adhesive. The lumen expands to fit over a guide wire positioned in the venous anatomy for the purpose of directing the lead to the site of implant. When the guide wire is removed, the lumen will collapse or fold down against the lead body 10. The distal end of the lumen may be closed, or a stop member 33 may be provided at the lumen distal end to prevent a stylet advanced within the lumen from extending beyond the lumen distal end and possibly damaging tissue.

According to yet another aspect of the invention, additional collapsible PTFE lumens as may be formed of PTFE tubing may be added around the lead body. Each of these tubes will further selectively promote tissue in-growth, and, may be positioned to urge one or more of the electrodes against tissue after the implant procedure. These additional lumens may further be used during an implant procedure in conjunction with a guidewire or stylet to steer a lead around a curve within the vascular system.

In one embodiment, the distal end of the lead body is sized to be positioned within a branch vein as a means of fixation. In this embodiment, the diameter of lead body 10 may range from approximately 0.030" to 0.090", and in a more specific embodiment may range from approximately 0.040" to 0.065". In such an embodiment, all electrodes have a diameter similar to that of the lead body to allow for placement of the lead within the coronary vessels.

FIG. 2 is a side cutaway view of one embodiment of the distal portion of the lead. The shocking electrode 16 of this embodiment is positioned between tip electrode 12 and ring electrode 18. This electrode may have a length in the range of approximately 2 to 4 cm and a shadow area in the range of 70 to 200 mm$^2$. The tip electrode 12 and ring electrode 18 may be spaced approximately 8 to 12 mm from either end of the shocking electrode in one embodiment of the invention. The length of the tip and ring electrodes may each range from approximately 4 to 10 mm, although other dimensions may also be utilized. Each electrode may having a surface area ranging from approximately 20 to 48 mm$^2$, although again, other sizes may be utilized Since the shocking electrode 16 is downsized to fit within a branch vein, the electrical coupling of the shocking electrode with either the tip electrode 12 or the ring electrode 18 provides additional current distribution during cardioversion/defibrillation to increase shocking efficacy. The entire surface of tip and ring electrodes may be conductive, however zones 50 and 52, respectively, may be provided on the surfaces of each electrode to create a more conductive and effective interface with the tissue for pacing. These zones, which may be annular, have specialized surfaces that may be of a porous and platinized platinum. The surfaces may also be steroid eluting, as described in U.S. Pat. No. 4,506,680 to Stokes, and related U.S. Pat. Nos. 4,577,642; 4,606,118; and 4,711,251, all commonly assigned to the assignee of the present invention and incorporated by reference herein in their respective entireties. Because the specialized zones 50 protrude radially from the tip and ring electrodes, these zones come into intimate contact with the heart wall when the lead is wedged within the confined space of a cardiac vein.

The conductors to each of these electrodes 21 and 25 may be connected directly to the end of the electrodes carrying this specialized surface 50 in order to maintain the best efficiency in delivering current to these zones for pacing. The length of specialized surface 50 may range from approximately 0.5 to 3 mm and the surface area from approximately 1 to 6 mm$^2$. Further, tip electrode 12 may have a tapered tip extending from the specialized zone 50. This tip adds to the shadow area of the electrode 12 in order to augment electrode 16 for high voltage shocking if this electrode is selected as the pacing anode. Moreover, if tip electrode is selected as the cathode, this tip does not drain excessive current when low voltage pacing pulses are delivered. Similarly, in the case of ring electrode 18, the portion 18a of the electrode may be a polished conductive surface that is less conductive and slightly smaller in diameter than ring 52. Portion 18a of ring electrode 18 may augment the electrode for high voltage shocking but does not drain excessive current from low voltage pacing pulses if ring electrode 18 is selected as the cathode.

In the embodiment shown in FIG. 2, the proximal portion 18a of ring electrode 18 may be formed of a coiled construction that provides better flexibility and strain relief over a longer length, so that the lead body may bend with less stress in the cardiac venous anatomy. The coil could be made of platinum or platinum clad tantalum or any material such as is known to the art and would be joined to the ring by a weld such as is known in the art.

The lead of the current invention may further include one or more radiopaque marker bands at the distal end such as marker band 53. This aids in placing the distal end of the lead during the implant procedure as discussed below.

Figure 3:
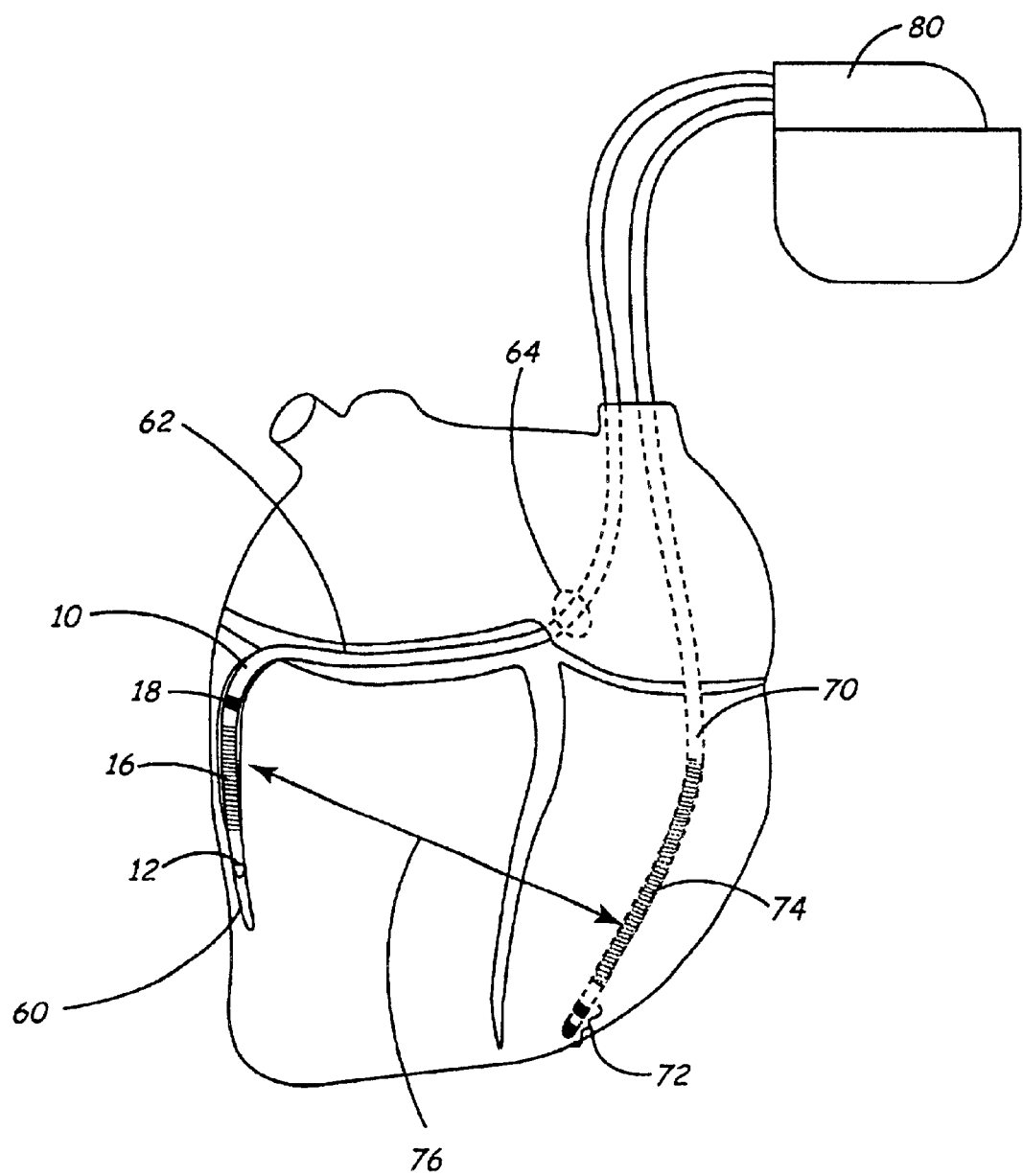
FIG. 3 is a posterior view of the heart illustrating the inventive lead system implanted within a branch vein of the coronary sinus.

FIG. 3 is a posterior view of the heart illustrating the inventive lead system implanted within a branch vein of the coronary sinus. Branch vein 60 may be any of the branch veins draining into the coronary sinus 62, including the posterior lateral vein (PLV), lateral vein, or great cardiac vein (GCV).

Positioning of the lead may be completed using several methods. During the implantation procedure, a guide catheter may be used to cannulate the ostium 64 (shown dashed) of coronary sinus 62. A guidewire may then be pre-loaded into side lumen 32, and the guidewire and lead may be delivered within the lumen of the guide catheter into the coronary sinus 62. Thereafter, the guidewire may be advanced beyond the distal tip of the lead and navigated into the selected branch vein. This process may be aided using fluoroscopy. A radiopaque marker such as marker 53 (FIG. 2) may be provided on a distal end of the guidewire and/or lead body 10 to aid in this process, for example. The guide catheter provides back up support for the navigation of the guide wire and lead during the location of the branch vein. After placement of the lead at the target location, the guidewire and guide catheter may then be removed from the body.

In another embodiment wherein the side lumen 32 includes a closed distal end, a stylet may be pre-loaded in the lumen, and the lead and stylet combination advanced within the lumen of the guide catheter to the coronary sinus 62. Thereafter, the stylet may be used to advance the lead distal end past the guide catheter distal end and into the desired branch vein. The guide catheter and stylet may then be removed from the body.

In yet another embodiment, the lead need not include a side lumen, but instead includes a lumen within the lead body, as may be defined via a coiled conductor in the manner discussed above. A stylet may be pre-loaded into this internal lumen so that the lead and stylet may be advanced into the coronary sinus in the manner discussed above, and thereafter positioned within a branch vein. According to yet another embodiment of the invention, the internal lead lumen may extend through the distal end of the lead, and a guidewire may be used to place the lead in a manner similar to that discussed above with respect to the side lumen. That is, after the guidewire and lead are positioned within the coronary sinus, the guidewire is advanced to subselect the branch vein, and the lead is then tracked over the guidewire to the target destination. The guidewire and guide catheter are thereafter removed from the body.

As shown in FIG. 3, the distal portion of the lead may be positioned with tip electrode 12 wedged into branch vein such that the shocking electrode 16 extends proximally along the vein and with ring electrode 18 positioned near the location where the branch vein drains into the coronary sinus. Another lead 70 having a pace/sense electrode pair 72 and a defibrillation coil 74 may be implanted in the right ventricular apex. When a high-voltage shock is deliver, current flows between defibrillation coils 16 and 74 along shock path 76. By electrically coupling either the tip electrode 12 or the ring electrode 18 to the defibrillation coil during the delivery of the shock, the current path may be widened to affect more tissue, increasing efficacy of the therapy.

After the leads are positioned within the patient, they may be coupled to an implantable medical device (IMD) 80. The implanting physician may then perform electrical testing to determine whether tip electrode 12 or ring electrode 18 provides the best location for biventricular pacing. Temporary contacts can be made with the connectors at the proximal end of the lead to test the most distal electrode 12 versus the most proximal electrode 18 as the cathode with the other two electrodes serving as the anode. Selection of the cathode is based on the efficiency of bi-ventricular pacing. This selection can be made by programming the pulse generator, or by providing a separate jumper connector to a pin grid array at the proximal end of the lead body 10.

Figure 4:
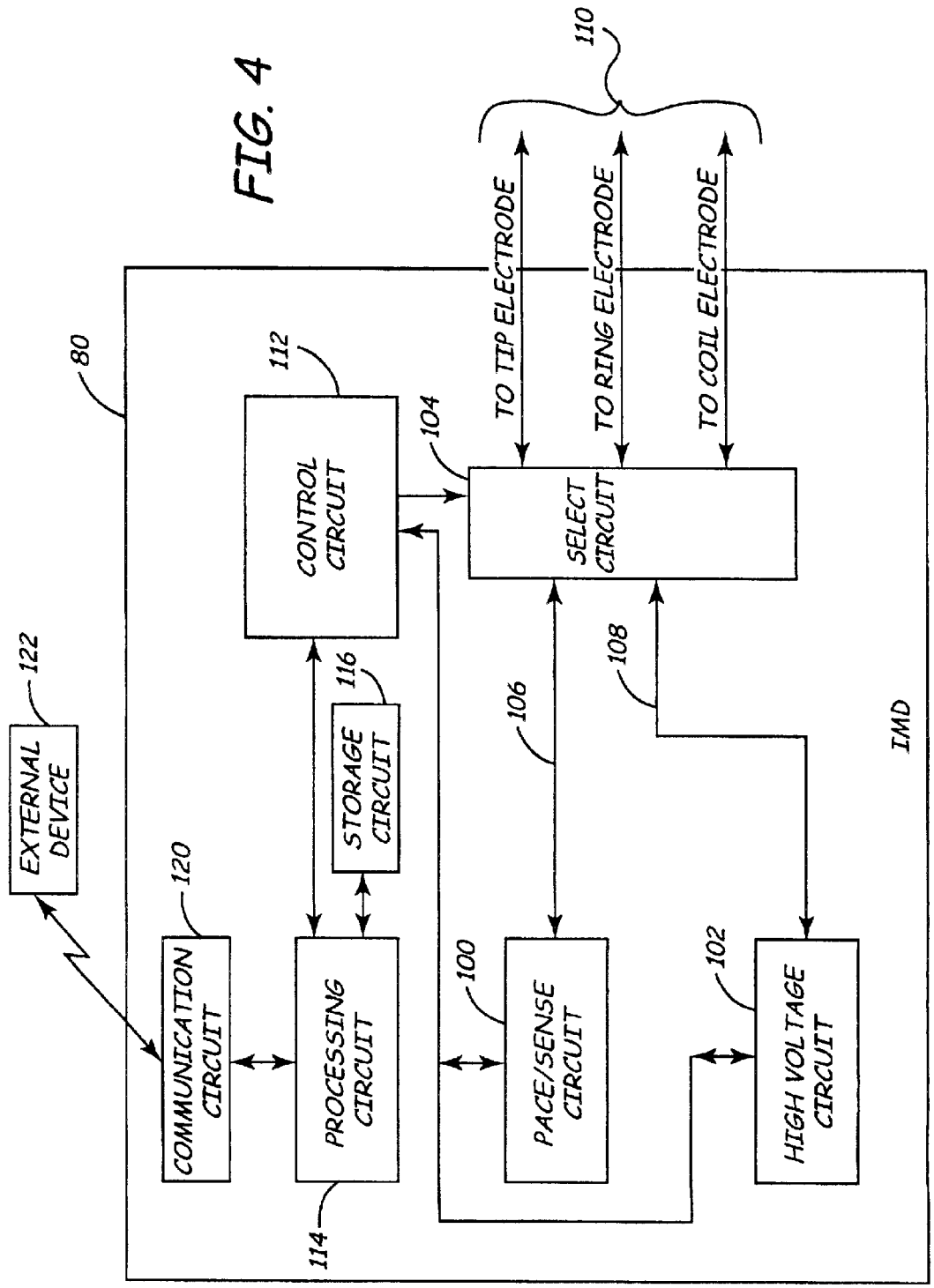
FIG. 4 is a block diagram of an IMD configuration including a programmable switch as may be used with the lead system of the current invention.

FIG. 4 illustrates an IMD configuration including a programmable switch as may be used with the lead system of the current invention. In this embodiment, IMD includes a pace/sense circuit 100 to deliver pacing pulses, and to sense cardiac signals. This circuit may include one or more output amplifiers and input amplifiers, and may be any of the configurations known in the art. This circuit may further include an analog-to-digital converter to convert sensed analog cardiac signals to digital signals. The IMD further includes a high-voltage circuit 102 for delivering high-voltage stimulation to a coil electrode such as shocking electrode 16. This circuit may include one or more high-voltage capacitors and/or charging circuits as is known in the art. The timing, voltage and current levels, and other parameters associated with pace/sense circuit 100 and high-voltage circuit 102 are controlled by control circuit 112.

Both the pace/sense circuit 100 and the high-voltage circuit 102 are coupled to a select circuit 104, which may be any combination of discrete components, integrated components, and/or one or more encoders and/or multiplexers. Additionally, or alternatively, Micro-Electrical-Mechanical systems (MEMs) technology may be incorporated within the switching circuit. MEMs switches are described in commonly-assigned U.S. patent application Ser. No. 10/004,025 filed Oct. 31, 2001 and incorporated herein by reference in its entirety. Select circuit 104 electrically couples lines 106 and 108 selectively to output lines 110. Select circuit 104 may be configured by control circuit 112.

IMD 80 further includes a processing circuit 114, which may be a microprocessor or another digital or analog processing circuit as is known in the art. Processing circuit 114 is coupled to storage circuit 116, which may include Random Access Memory (RAM), Read-Only Memory (ROM), and/or any other type of storage circuit known in the art. This storage circuit may store operational parameters such as stimulation parameters, and/or programmed instructions executed by processing circuit 116. Processing circuit 116 may further be coupled to a communication circuit 120, which may be a telemetry circuit for performing wireless communication transfers to an external device 122. External device may be a programmer, or any other type of external device for monitoring, programming, or in any other way interacting within IMD 80.

As described above, after lead implantation is completed, a physician may conduct testing to determine whether the tip electrode 12 or ring electrode 18 are associated with better pacing thresholds, and should therefore be selected as the cathode. After this determination is complete, control circuit 112 can be programmed to configure select circuit 104 so that signals lines shown collectively as line 106 are coupled to output lines 110 to achieve the desired configuration. The programming of control circuit 112 can be accomplished via a communication transfer from external device 122 to communication circuit 120, and, in the current embodiment, a subsequent transfer of configuration data from processing circuit 116 to control circuit 112. Similarly, prior to the delivery of a high-voltage shock, control circuit 112 may configure select circuit 104 such that either the tip or ring electrode are electrically coupled to shocking electrode 16 to thereby increase the shadow area of this electrode, and, in turn, maximize the tissue area affected by the delivered current. This coupling of tip or ring electrode to shocking electrode 16 may be performed during pacing therapy as well, if desired, such that the shocking electrode serves as an anode.

In another embodiment of the invention, the coupling of electrodes may be performed at the connector module instead of via an electronic circuit within IMD 80. According to this embodiment, the coupling configuration of electrodes is not generally adapted to be modified during therapy delivery, as is discussed below.

FIG. 5 is a side view of a lead that is similar to that shown in FIG. 2 including a multi-pin connector as may be used with the current invention. The lead is shown to include three conductors 21, 23, and 25, each coupled to a respective electrode in the manner discussed above. These conductors may be any type known in the art, including cable or coil conductors. Each of the conductors is electrically coupled to a respective connector pin of connector 140. For example, shocking conductor 23 is coupled to pin 146, conductor 21 is coupled to pin 142, and conductor 25 is coupled to a third pin (not shown in FIG. 5.) FIG. 5 further shows a lockout member 149 to be discussed further below.

FIG. 6 is an end view of connector 140, illustrating connection members shown as pins 142, 146, and additional pin 148, which is electrically coupled to conductor 25. This view further illustrates lockout feature 149. In this embodiment, the pins of connector 140 are equidistant from one another. These pins may be joined to a mating interface on a connector assembly in several different orientations, as illustrated in FIGS. 7 and 8.

FIG. 7 is an end view of a mating interface 160 for use with connector 140 of FIG. 6. The mating interface includes a first port 162 that is circular to receive the pin that is electrically coupled to the electrode selected to be the cathode. As discussed above, since either tip electrode 12 or ring electrode 18 will be selected as the cathode, first port 162 will therefore be coupled to either pin 142 or 148. The second port 164 is oblong, and is designed to mate with, and electrically couple to, the remaining two pins. That is, port 164 will receive either pins 146 and 142, or pins 146 and 148. The two options are shown by dashed lines 150 of FIG. 6. Lockout member 149 may optionally be provided as a protruding ridge between pins 142 and 148 to prevent mating interface 160 from receiving the combination of pins 142 and 148, since this would select shocking electrode 16 as the pacing cathode, with the remaining two electrodes selected to deliver high-voltage shocks.

Figure 8:
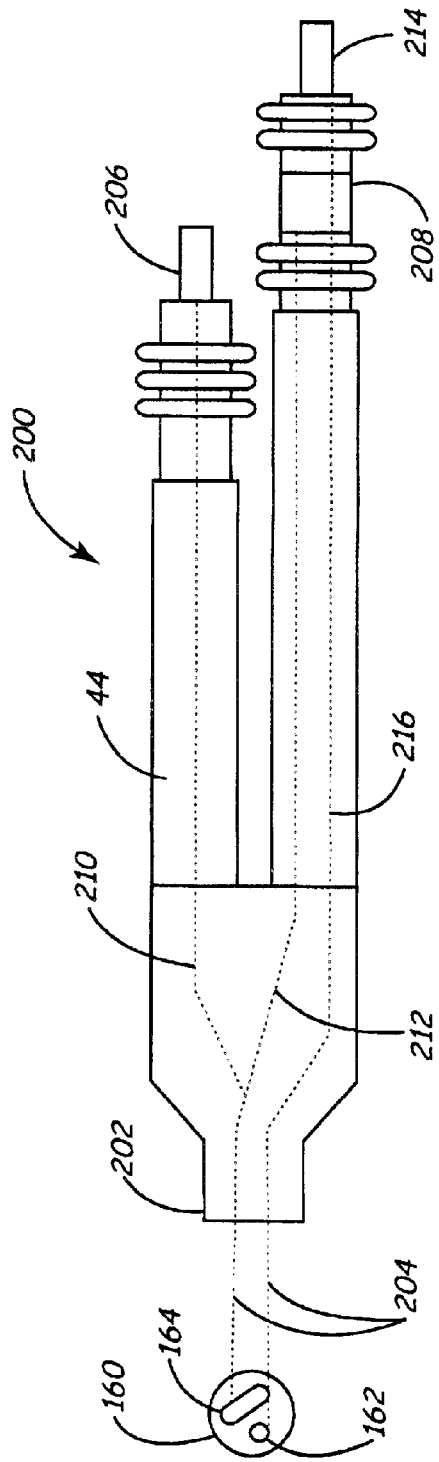
FIG. 8 is a side view illustrating use of the mating interface of FIG. 7 incorporated within an adapter that includes a standard DF-1 connector.

FIG. 8 is a side view illustrating use of mating interface 160 incorporated within an adapter that includes a standard DF-1 connector 200 at the proximal end. Mating interface 160 is shown in cross-section to illustrate the various electrical connections associated with the adapter, although it will be appreciated that this mating interface is actually included within a distal end 202 of the adapter.

Dashed lines 204 illustrate the electrical connections associated with the ports of mating interface 160. Port 164 is electrically coupled to connector pin 206 and ring connector 208 of adapter via conductors 210 and 212, respectively. Similarly, port 162 is electrically coupled to pin connector 214 via conductor 216. By selectively coupling port 162 to either pin 142 or 148 of connector 140, then coupling pins 206 and 208 to a connector block of a pacemaker cardioversion/defibrillator as is known in the art, the desired electrical connections as determined by threshold testing may be obtained. A high-voltage shock may then be delivered via pin 206 and conductor 210, whereas pacing therapy may be delivered via pin 214, with the return current path being provided by pin connector 206 and ring connector 208.

Figure 9:
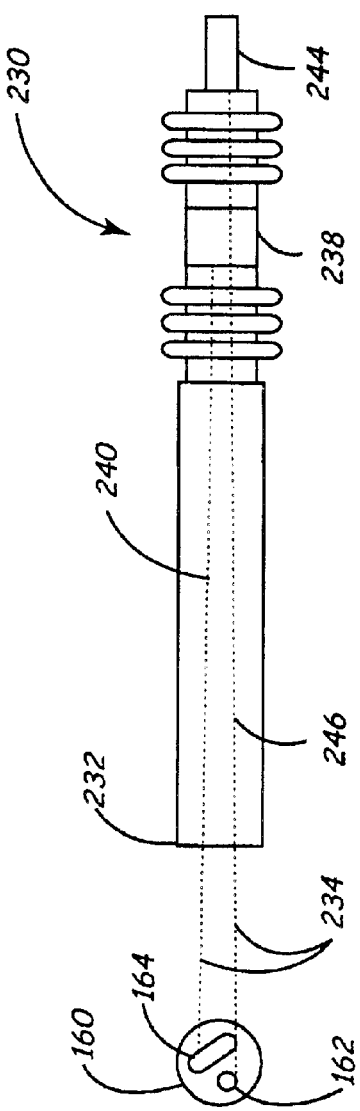
FIG. 9 is a side view illustrating use of mating interface incorporated within an adapter that includes a standard IS-1 connector.

FIG. 9 is a side view illustrating use of mating interface 160 incorporated within an adapter that includes a standard IS-1 connector 230 at the proximal end. As with FIG. 8, mating interface 160 is shown in cross-section to clarify the electrical connections, and it will be appreciated the mating interface is actually included within the distal end 232 of adapter. Dashed lines 234 illustrate the electrical connections associated with mating interface 160. Port 164 is electrically coupled to ring connector 238 of adapter via conductor 240. Similarly, port 162 is electrically coupled to pin connector 244 via conductor 246. By selectively coupling port 162 to either pin 142 or pin 148 of connector 140, then coupling pin connector 246 and ring connector 238 to a connector block of a pacemaker as known in the art, the desired electrical connections as determined by threshold testing may be obtained. In this embodiment, pacing therapy may be delivered via pin 244, with the return current path being provided by ring connector 238. As will be appreciated, in this embodiment, shocking electrode 16 (FIG. 1) is used only as the anode for pacing therapy, and is not utilized to delivery high-voltage therapy.

Although FIGS. 8 and 9 contemplate the use of adapters that include industry-standard connectors such as IS-1 and DF-1 connections, this need not be the case, and any type of industry-standard or non-standard connector may employ the mating interface 160.

Figure 10:
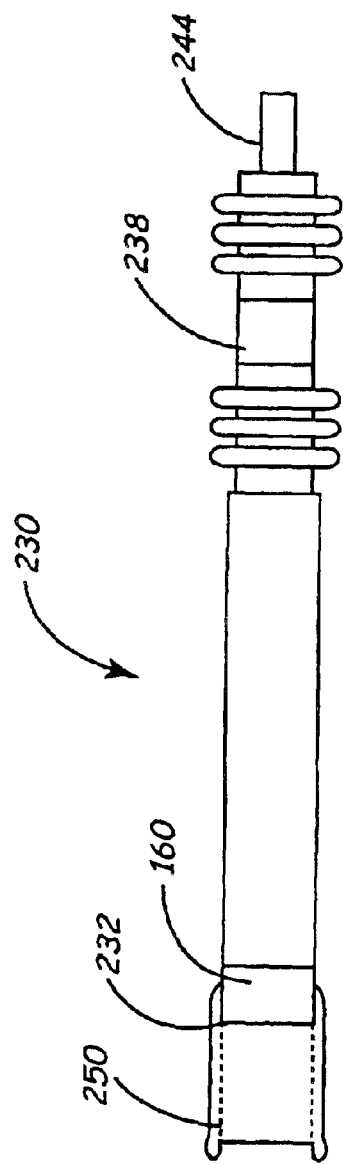
FIG. 10 illustrates an adapter as shown in FIG. 9 coupled to a lead including the connector shown in FIG. 5.

FIG. 10 is a side view of an adapter that is similar to that shown in FIG. 9, and which further includes a roll-back sleeve 250. This sleeve may be formed of a flexible, biocompatible polymer such as silicone or polyurethane, and is rolled over the proximal end of a lead such as a lead shown in FIG. 5. This forms a hermetic seal that prevents fluid ingress around the connector pins of connector 140 and the ports of mating interface 160.

Figure 11:
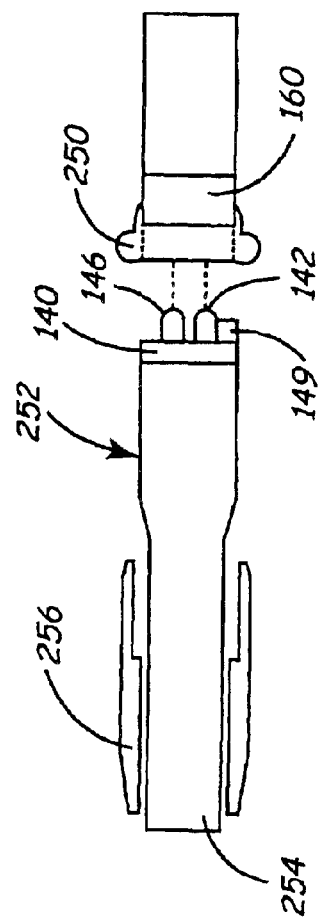
FIG. 11 illustrates an adapter such as shown in FIG. 9 being coupled to a lead of a type as shown in FIG. 5.

FIG. 11 illustrates an adapter such as shown in FIG. 9 being coupled to a lead 254 of a type as shown in FIG. 5. In this view, roll-back sleeve 250 is in a folded, or "rolled-back", position to allow for easy connection between connector 140 and mating interface 160. After this connection is made, roll-back sleeve is unfolded to a position similar to that shown in FIG. 10. In this position, roll-back sleeve extends over connector 140, and further over the proximal end 252 of lead 254. Also shown in FIG. 11 is an optional suture sleeve 256 coupled to lead 254 to allow the sleeve to be sutured to tissue so that lead position is maintained at the lead proximal end.

As noted above, to determine the optimal configuration for a lead according to the current invention, threshold testing must be performed. During this testing, various pins of connector 140 must be temporarily coupled. This can be accomplished using adaptors having clips similar to "alligator" clips.

Figure 12:
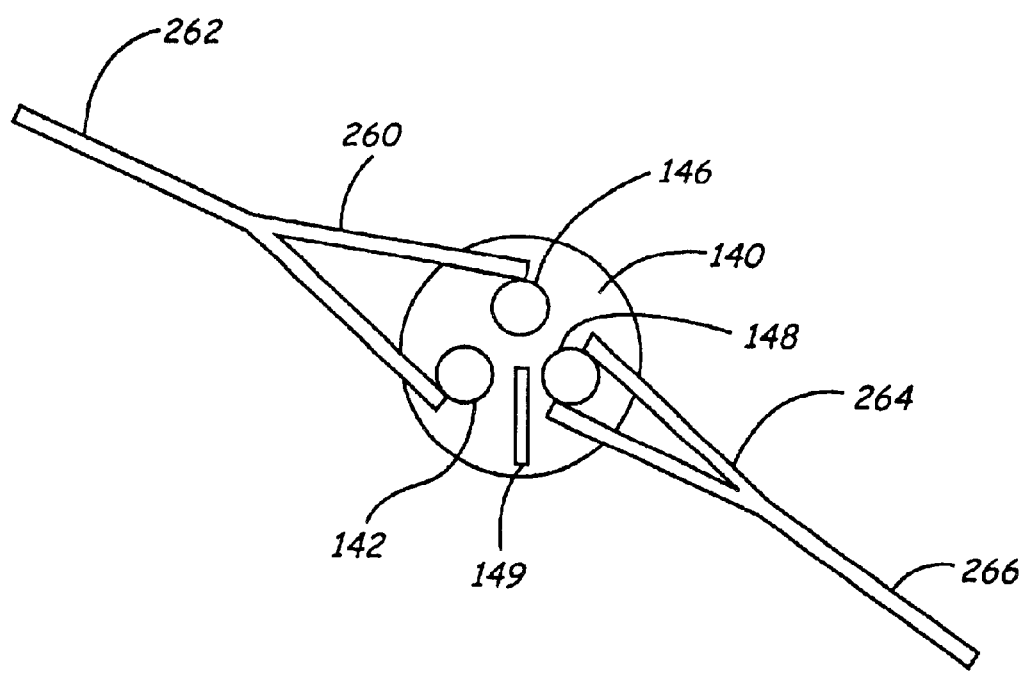
FIG. 12 is an end view of the connector of FIG. 5 being temporarily configured for threshold testing.

FIG. 12 is an end view of connector 140 showing temporary electrical coupling of pin 146 to pin 142 using a clip 260. Clip 260 is coupled to a distal end of lead 262. Proximal end of lead 262 (not shown) may be coupled to pulse generation equipment suitable for performing threshold testing during the implant procedure. Similarly, clip 264 is temporarily coupled to pin 148 so that proximal end of lead 266 may be coupled to pulse generation equipment for testing purposes.

The above-described invention provides an improved system for stimulating the left side of the heart. It will be appreciated that other modifications and adaptations within the scope of the invention may be contemplated by those skilled in the art. Therefore, the above discussion are to be considered exemplary in nature, and not limiting.

What is claimed is:

1. A medical electrical lead to provide electrical stimulation to a heart, comprising:
   an elongated lead body having a proximal portion and a distal portion;
   a first pacelsense electrode coupled to the distal portion adapted to provide stimulation to a left chamber of the heart;
   a coil electrode coupled to the distal portion proximal to the first pace/sense electrode adapted to provide cardioversion/defibrillation stimulation; and
   a second pace/sense electrode coupled to the distal portion and being proximal to the coil electrode,
   wherein the elongate lead body provides at least one lumen extending at least a portion of the length of the elongate lead body, the at least one lumen includes a lumen adjacent to an exterior surface of the lead body, and the lumen adjacent to the exterior surface of the lead body is formed of a collapsible tube.

2. The lead of claim 1, and further including a connector coupled to the proximal portion to allow either the first or the second pace/sense electrode to be selected as a cathode for delivery of relatively low-voltage stimulation to the left chamber of the heart.

3. The lead of claim 2, wherein the connector is adapted to allow the other of either the first or the second pace/sense electrode to be electrically coupled to the coil electrode.

4. The lead of claim 1 wherein the lumen adjacent to the exterior surface of the lead body is closed at the distal end.

5. The lead of claim 1, and further including a stop member proximate the distal end of the lumen adjacent to the exterior surface of the lead body.

6. The lead of claim 1, wherein the second pace/sense electrode is a coil electrode.

7. The lead of claim 1, wherein the first pace/sense electrode is a tip electrode coupled to the distal tip of the elongate lead body.

8. The lead of claim 7, wherein the tip electrode includes a tapered tip.

9. The lead of claim 1, wherein at least one of the first and the second pace/sense electrodes includes a zone protruding from the surface of the first and the second pace/sense electrodes to couple to tissue.

10. The lead of claim 9, wherein the zone is a protruding annular ring.

11. A medical electrical lead to provide electrical stimulation to a heart, comprising:
    an elongated lead body having a proximal portion and a distal portion;
    a first pace/sense electrode coupled to the distal portion adapted to provide stimulation to a left chamber of the heart;
    a coil electrode coupled to the distal portion proximal to the first pace/sense electrode adapted to provide cardioversion/defibrillation stimulation; and
    a second pace/sense electrode coupled to the distal portion and being proximal to the coil electrode, wherein the elongate lead body has at least one portion of en exterior surface including a porous Polytetrafluoroethylene (PTFE) material.

12. The lead of claim 11, wherein the at least one portion is located proximate to any of the first or the second pace/sense electrodes or the coil electrode.

13. A system for providing electrical stimulation to a heart, comprising:
    an elongated lead body having a proximal portion and a distal portion;
    a first pace/sense electrode coupled to the distal portion adapted to pace a left chamber of the heart;
    a coil electrode coupled to the distal portion proximal to the first pace/sense electrode adapted to provide cardioversion/defibrillation stimulation to the heart;
    a second pace/sense electrode coupled to the distal portion and positioned proximal to the coil electrode;
    a connector coupled to the proximal portion to allow either the first or the second pace/sense electrode to be selected as a cathode to deliver relatively low-voltage electrical stimulation to the left chamber of the heart, wherein the connector is adapted allow the other of either the first or the second pace/sense electrode to be electrically coupled to the coil electrode; and
    an adapter to couple to the connector to select either the first or the second pace/sense electrode as a cathode for delivery of the relatively low-voltage electrical stimulation, wherein the adapter includes a roll-back sleeve.

14. The system of claim 13, and further including an implantable medical device (IMD) to electrically couple to at least two electrodes selected from the group consisting of the first and the second pace/sense electrodes and the coil electrode.

15. The system of claim 14, wherein the IMD includes a select circuit to select either the first or the second pace/sense electrode as a cathode for delivery of the relatively low-voltage electrical stimulation.

16. The system of claim 15, wherein the select circuit includes a circuit to select the other of the first or the second pace/sense electrode as an anode for delivery of the relatively low-voltage electrical stimulation.

17. The system of claim 16, wherein the select circuit includes a circuit to electrically couple the other of the first or the second pace/sense electrode to the coil electrode.

18. The system of claim 13, wherein the adapter is adapted to select the other of the first or the second pace/sense electrode as en anode for delivery of the relatively low-voltage electrical stimulation.

19. The system of claim 18, wherein the adapter is adapted to electrically couple the other of the first or the second pace/sense electrode to the coil electrode.

20. The system of claim 18, wherein the adapter includes a standard IS-1 connector.

21. The system of claim 19, wherein the adapter includes a standard DF-1 connector.

22. The system of claim 13, wherein the connector includes at least three connection members adapted to be received by the adapter.

23. The system of claim 22, wherein each of the at least three connection members are spaced substantially equidistantly from the other of the at least three connection members.

24. A system for providing electrical stimulation to a heart, comprising:
    an elongated lead body having a proximal portion and a distal portion;
    a first pace/sense electrode coupled to the distal portion adapted to pace a left chamber of the heart;
    a coil electrode coupled to the distal portion proximal to the first pace/sense electrode adapted to provide cardioversion/defibrillation stimulation to the heart; and
    a second pace/sense electrode coupled to the distal portion and positioned proximal to the coil electrode;
    a connector coupled to the proximal portion to allow either the first or the second pace/sense electrode to be selected as a cathode to deliver relatively low-voltage electrical stimulation to the left chamber of the heart, wherein the connector is adapted to allow the other of either the first or the second pace/sense electrode to be electrically coupled to the coil electrode; and an adapter to couple to connector to select either the first or the second pace/sense electrode as a cathode for delivery of the relatively low-voltage electrical stimulation, wherein the connector includes at least three connection members adapted to be received by the adapter, and wherein the adapter includes a first port to couple to two of the at least three connection members, and a second port to couple to one of the at least three connection members.

25. The system of claim 24, wherein the adapter includes a lockout member to prevent a predetermined two of the at least three connection members from coupling to the first port.

26. A method of delivering electrical stimulation to a heart, comprising the steps of:
   a.) delivering a lead to a branch vein of the coronary sinus, wherein the lead comprises:
      an elongated lead body having a proximal portion and a distal portion;
      a first pace/sense electrode coupled to the distal portion; and
      a second pace/sense electrode coupled to the distal portion and positioned proximal to the first pace/sense electrode;
   b.) selecting one of the first or the second pace/sense electrode as a cathode and the other of the first or the second pace/sense electrode as the anode; and
   c.) delivering relatively low-voltage electrical stimulation between the cathode and the anode to a left chamber of the heart, wherein the lead includes a lumen, and wherein step a.) includes guiding the lead with a delivery device positioned within the lumen, and wherein the lumen is a collapsible tube adjacent to an exterior surface of the lead.

27. The method of claim 26, wherein the lead further comprises a coil electrode coupled to the distal portion and positioned proximal the first pace/sense electrode and distal to the second pace/sense electrode, and further comprising:
   electrically coupling the other of the first or the second pace/sense electrode to the coil electrode prior to step c.).

28. The method of claim 27, and further including delivering relatively high-voltage electrical stimulation via the coil electrode.

29. The method of claim 28, wherein the step of delivering relatively high-voltage electrical stimulation via the coil electrode is performed after electrically coupling the other of the first or the second pace/sense electrode to the coil electrode.

30. The method of claim 26, and further including coupling an implantable medical device (IMD) to the lead, wherein the IMD includes a select circuit, and wherein step b.) includes configuring the select circuit.

31. The method of claim 24, wherein step b.) includes coupling the lead to an adapter.

32. The method of claim 26, wherein the tube is formed of porous PTFE material.

33. The method of claim 26, wherein the delivery device is a stylet.

34. The method of claim 26, wherein the delivery device is a guidewire.

* * * * *

UNITED STATES PATENT AND TRADEMARK OFFICE
CERTIFICATE OF CORRECTION

PATENT NO. : 6,901,289 B2
APPLICATION NO. : 10/034905
DATED : May 31, 2005
INVENTOR(S) : Roger W. Dahl et al.

It is certified that error appears in the above-identified patent and that said Letters Patent is hereby corrected as shown below:

Column 11, line 6, delete "first pacelsense" and insert --first pace/sense--

Column 12, line 11, delete "adapted allow" and insert --adapted to allow--

Column 12, line 37, delete "en anode" and insert --an anode--

Column 11, line 29, delete "claim 1" and insert --claim 8--

Signed and Sealed this

Second Day of January, 2007

JON W. DUDAS
*Director of the United States Patent and Trademark Office*